(12) United States Patent
Truitt et al.

(10) Patent No.: US 8,688,184 B2
(45) Date of Patent: Apr. 1, 2014

(54) NONINVASIVE PHOTOPLETHYSMOGRAPHIC SENSOR PLATFORM FOR MOBILE ANIMALS

(75) Inventors: Patrick Truitt, Murrysville, PA (US); Bernard F. Hete, Kittanning, PA (US); Eric W Starr, Allison Park, PA (US)

(73) Assignee: Starr Life Sciences Corporation, Oakmont, PA (US)

( * ) Notice: Subject to any disclaimer, the term of this patent is extended or adjusted under 35 U.S.C. 154(b) by 1513 days.

(21) Appl. No.: 12/330,501

(22) Filed: Dec. 8, 2008

(65) Prior Publication Data

US 2009/0149727 A1 Jun. 11, 2009

Related U.S. Application Data

(60) Provisional application No. 60/992,880, filed on Dec. 6, 2007, provisional application No. 61/108,010, filed on Oct. 23, 2008.

(51) Int. Cl.
*A61B 5/00* (2006.01)

(52) U.S. Cl.
USPC .......................................... 600/323; 600/344

(58) Field of Classification Search
USPC .......................................................... 600/344
See application file for complete search history.

(56) References Cited

U.S. PATENT DOCUMENTS

| | | | |
|---|---|---|---|
| 4,572,197 A | 2/1986 | Moore et al. | |
| 4,863,265 A | 9/1989 | Flower et al. | |
| 5,005,573 A | 4/1991 | Buchanan | |
| 5,851,178 A | 12/1998 | Aronow | |
| 5,991,648 A * | 11/1999 | Levin | 600/344 |
| 6,014,576 A | 1/2000 | Raley | |
| 6,062,224 A * | 5/2000 | Kissinger et al. | 128/897 |
| 6,657,544 B2 | 12/2003 | Barry et al. | |
| 6,830,013 B2 | 12/2004 | Williams | |
| 8,073,518 B2 * | 12/2011 | Chin | 600/344 |
| 2002/0010390 A1 | 1/2002 | Guice et al. | |
| 2005/0065414 A1 * | 3/2005 | Allen et al. | 600/310 |
| 2006/0258914 A1 * | 11/2006 | Derchak et al. | 600/300 |
| 2007/0073119 A1 * | 3/2007 | Wobermin et al. | 600/323 |
| 2008/0132770 A1 * | 6/2008 | Ayers et al. | 600/323 |

OTHER PUBLICATIONS

L. Nagl1, R. Schmitz, S. Warren, T.S. Hildreth, H. Erickson, and D. Andresen, Wearable Sensor System for Wireless State-of-Health Determination in Cattle,Engineering in Medicine and Biology Society, 2003. Proceedings of the 25th Annual International Conference of the IEEE, published Apr. 5, 2004, vol. 4, On pp. 3012-3015 vol. 4, Department of Computing and Information Sciences, Kansas State University, Manhattan, KS, USA, http://people.cis.ksu.edu/~dan/Vet_Cancun_BMOO_Final.pdf.

\* cited by examiner

*Primary Examiner* — Brian Szmal
*Assistant Examiner* — H. Q. Nguyen
(74) *Attorney, Agent, or Firm* — Blynn L. Shideler; Krisanne Shideler; BLK Law Group (57) ABSTRACT

A noninvasive photoplethysmographic sensor platform for mobile animals such as small rodents, namely rats and mice is useful such as in a laboratory research environment. The noninvasive photoplethysmographic sensor platform may be a collar which provides an easily affixed, adjustable attachment mechanism that encircles the animal, such as the neck. The neck of the animal provides several particular advantages as a sensor mounting platform for photoplethysmographic sensors. For pulse oximetry, the neck location will provide significant blood flow under all conditions. For small mammals, such as rats and mice, transmittance pulse oximetry through the neck of the subject remains possible. The neck mounted collar also offers inherent bite resistance to the sensor platform.

13 Claims, 3 Drawing Sheets

NONINVASIVE PHOTOPLETHYSMOGRAPHIC SENSOR PLATFORM FOR MOBILE ANIMALS

RELATED APPLICATIONS

The present invention claims priority of U.S. Provisional Patent Application Ser. No. 61/108,010 entitled "Neck Collar Clip Small Animal Pulse Oximetry Sensor" filed Oct. 23, 2008.

The present invention claims priority of U.S. Provisional Patent Application Ser. No. 60/992,880 entitled "Noninvasive Photoplethysmographic Sensor Platform For Mobile Animals" filed Dec. 6, 2007.

BACKGROUND OF THE INVENTION

1. Field of the Invention

The present invention relates to photoplethysmographic readings for animal research and more particularly, the present invention is directed to a noninvasive photoplethysmographic sensor platform for mobile animals such as small rodents.

2. Background Information

A photoplethysmograph is an optically obtained plethysmograph, which, generically, is a measurement of changes in volume within an organ whole body, usually resulting from fluctuations in the amount of blood or air that the organ contains. A photoplethysmograph is often obtained by using a pulse oximeter. A conventional pulse oximeter monitors the perfusion of blood to the dermis and subcutaneous tissue of the skin. Pulse oximetry is a non invasive method that allows for the monitoring of the oxygenation of a subject's blood, generally a human or animal patient or an animal (or possibly human) research subject. The patient/research distinction is particularly important in animals where the data gathering is the primary focus, as opposed to care giving, and where the physiologic data being obtained may, necessarily, be at extreme boundaries for the animal.

As a brief history of pulse oximetry, it has been reported that in 1935 an inventor Matthes developed the first 2-wavelength earlobe $O_2$ saturation meter with red and green filters, later switched to red and infrared filters. This was the first device to measure $O_2$ saturation. Further in 1949 an inventor Wood added a pressure capsule to squeeze blood out of the earlobe to obtain zero setting in an effort to obtain absolute $O_2$ saturation value when blood was readmitted. The concept is similar to today's conventional pulse oximetry but suffered due to unstable photocells and light sources and the method was not used clinically. In 1964 an inventor Shaw assembled the first absolute reading ear oximeter by using eight wavelengths of light which was commercialized by Hewlett Packard. This use was limited to pulmonary functions due to cost and size. Effectively, modern pulse oximetry was developed in 1972, by Aoyagi at Nihon Kohden using the ratio of red to infrared light absorption of pulsating components at the measuring site, and this design was commercialized by BIOX/Ohmeda in 1981 and Nellcor, Inc. in 1983. Prior to the introduction of these commercial pulse oximeters, a patient's oxygenation was determined by a painful arterial blood gas, a single point measure which typically took a minimum of 20-30 minutes processing by a laboratory. It is worthy to note that in the absence of oxygenation, damage to the human brain starts in 5 minutes with brain death in a human beginning in another 10-15 minutes. Prior to its introduction, studies in anesthesia journals estimated US patient mortality as a consequence of undetected hypoxemia at 2,000 to 10,000 deaths per year, with no known estimate of patient morbidity. Pulse oximetry has become a standard of care for human patients since about 1987.

Pulse oximetry has been a critical research tool for obtaining associated physiologic parameters in humans and animals beginning soon after rapid pulse oximetry became practical.

In pulse oximetry a sensor is placed on a thin part of the subject's anatomy, such as a human fingertip or earlobe, or in the case of a neonate, across a foot, and two wavelengths of light, generally red and infrared wavelengths, are passed from one side to the other. Changing absorbance of each of the two wavelengths is measured, allowing determination of the absorbance due to the pulsing arterial alone, excluding venous blood, skin, bone, muscle, fat, etc. Based upon the ratio of changing absorbance of the red and infrared light caused by the difference in color between oxygen-bound (bright red) and oxygen unbound (dark red or blue, in severe cases) blood hemoglobin, a measure of oxygenation (the percent of hemoglobin molecules bound with oxygen molecules) can be made.

The measured signals of pulse oximeters are also utilized to determine other physical parameters of the subjects, such as heart rate (pulse rate). Starr Life Sciences, Inc. has utilized pulse oximetry measurements to calculate other physiologic parameters such as breath rate, pulse distension, and breath distention, which can be particularly useful in various research applications.

Regarding human and animal pulse oximetry, the underlying theory of operation remains the same. However, consideration must be made for the particular subject or range of subjects in the design of the pulse oximeter, for example the sensor must fit the desired subject (e.g., a medical pulse oximeter for an adult human finger simply will not adequately fit onto a mouse finger or paw; and regarding signal processing the signal areas that are merely noise in a human application can represent signals of interest in animal applications due to the subject physiology). Consequently there can be significant design considerations in developing a pulse oximeter for small mammals or for neonates or for adult humans, but, again the underlying theory of operation remains substantially the same.

In addressing animal pulse oximetry, particularly for small rodents, one approach has been to modify existing human or neonate oximeters for use with rodents. This approach has proven impractical as the human based systems can only stretch so far and this approach has limited the use of such adapted oximeters. For example, these adapted human oximeters for animals have an upper limit of heart range of around 400 or 450 beats per minute which is insufficient to address mice that have a conventional heart rate of 400-800 beats per minute. Starr Life Sciences has designed a small mammal oximeter from the ground up, rather than an adapted human model, that has effective heart rate measurements up to 900 beats per minute, and this is commercially available under the Mouse Ox™ oximeter brand since 2005.

In the field of pulse oximetry in humans, U.S. Pat. No. 5,005,573 discloses an oximetry device in an endotracheal tube to enable "more accurate" and "more quickly responsive" oximetry measurements to be made through the patient's neck an to enable continual monitoring of the tube position within the trachea. Although this placement can provide improved oximetry measurements, it is much more invasive than conventional external pulse oximeters that have been placed on human fingers, toes and earlobes. Futher, endotracheal tube placement is impractical or mobile animal studies and for studies of small animals such as rodents (e.g. mice and rats).

U.S. Pat. No. 4,572,197 discloses a vest for positioning medical instrumentation about the human or, in theory, animal torso to provide ambulatory monitoring of patient cardiac functions.

In animal fields, neck collars have served as a mounting platform for selected sensors, such as bark sensors or position sensors in animal control collars that direct a pressure pulse wave to an animal as a negative stimulus to deter undesired behavior (e.g. shock), such as described in U.S. Pat. No. 6,830,013. Other animal control collars use a collar mounted sensor sensing a perimeter wire for animal control, see U.S. Pat. No. 6,657,544 and also products sold under the Invisible Fence® brand name.

In wildlife research, collars are the most common form of transmitter attachment for mammals in radio-telemetry studies, often wildlife studies. The following discussion offers background information on such radio-telemetry collar mounting considerations. Collars should be made of materials which are durable; are comfortable and safe for the animal; can withstand extreme environmental conditions; do not absorb moisture; and maintain their flexibility in low temperatures. Common collar materials for transmitter mounting in radio-telemetry based studies are butyl belting, urethane belting, flat nylon webbing, tubular materials, metal ball-chains, PVC plastic, brass or copper wire and cable ties. The transmitter package may be situated either under the animal's neck or on top of it. Collars must be properly fitted for the comfort and safety of the animal. A collar should fit snugly to prevent it coming off or chafing the animal as it moves, but it must also be sufficiently loose as to be comfortable and not interfere with swallowing or panting. To reduce the risk of chafing on the neck, collars should generally be fastened at the side, with any metal fittings covered or smoothed on the inside surface of the collar. Neck circumference will vary according to species, age, sex and sometimes the season. Transmitter manufacturers usually have records of collar sizes previously used for various species. Collar thickness and width are important considerations. Width of the collar will affect how the transmitter sits on the animal's neck. Some researchers prefer narrower collars because there is less surface area in contact with the animal. Others prefer wider collars for better weight distribution. One of the most important considerations should be the possibility of the collar getting caught up in vegetation. This is a particularly important consideration with small mammals (especially those that burrow). Expandable collars and harnesses are mandatory in those cases where it is necessary to allow for growth in young animals or for species which undergo neck swelling. Braided nylon over surgical tubing and nylon web with elastic folds are offered as expandable collars by one company. Expandable collars should not be used unless they are well tested, as poorly designed collars can be very problematic. In the past, certain collars have stretched prematurely as a result of social interactions or behaviors such as neck rubbing. As a result, there is always the possibility of transmitter loss, icing up in winter, or of the collar becoming snagged by branches or even the animal's own legs. Breakaway or "rot-away" collars are strongly recommended in cases where the researcher does not intend to recapture the animal and remove the collar. Breakaway collars or harnesses incorporate a link of material which is designed to break away and allow the transmitter to drop off after a pre-determined interval. Breakaway links should be environmentally degradable material or electronic links controlled by timers or radio receivers. Environmentally degradable materials which have been used for this purpose include cotton thread and sections of cotton fire hose or cotton spacers on large mammal collars. These weak links may also function to break and free the animal if the collar/harness is snagged on a branch. However, it is important to consider that the breakaway collar or harness does not impair the movement or activities of the animal during the period in which it is being shed. For example, a breakaway bird body harness could easily impair wing movement as it is lost and result in mortality. Radio and timer-controlled breakaways may be jammed by freezing or dirt, and also add to the size, weight and complexity of the transmitter package. Where appropriate, it is recommended that collars and harnesses be marked in order to enhance their visibility. Paint or non-metallic reflective materials may be sewn or glued to collars and harnesses; however, this is likely not appropriate for cryptic species. Metallic tape or foils should not be used as they will detune the transmitting antenna. Adhesive tapes should also not be used as they are not very durable and may foul fur or feathers. For game species or urban studies it may also be helpful to mark a contact phone number on the collar. Color-coded collars are also available from telemetry equipment manufacturers. VHF temperature sensors may be used to monitor either the animal's body temperature or the environmental temperature. Body temperature data may be useful in determining health or reproductive status, and ambient temperature may also be utilized for habitat selection or hibernation studies. Transmitters for body temperature may be placed subcutaneously, internally, within the inner ear, anally, or vaginally. Transmitters for ambient or den temperature may be placed on a regular collar or harness. Size or weight limitations and the data precision required will also affect transmitter type and placement.

A 2003 study at Kansas State University entitled "Wearable Sensor System for Wireless State-of-Health Determination in Cattle" disclosed a collection of sensors for animal research which was designed to incorporate off-the-shelf and custom-designed sensors and modules to provide cost-effective animal health monitoring capabilities. These sensors and modules included a GPS (Global Positioning System) unit, a pulse oximeter, a core body temperature sensor, an electrode belt, a respiration transducer, and an ambient temperature transducer. A GPS collar unit was intended to yield both animal location and movement data. A commercial CorTemp system was intended to monitors core body temperature continuously via an ingestible bolus. The bolus wirelessly transmitted temperature data to a receiving unit connected to BMOO. The animal was also to wear a Polar electrode belt that acquires pulse rate and transmits it wirelessly to the core body temperature receiving unit. A custom-designed pulse oximeter was proposed to measure blood oxygen saturation and pulse rate from an ear tag that the animal would wear. It is interesting to note that in this attempt for pulse oximetry in cattle, off the shelf human oximeters, were insufficient and a custom design was required.

Some invasive sensor proposals have been made for animal research including U.S. Patent Application Publication No. 2002-0010390 that discloses an Automated Animal Health Monitoring System (AAHMS) for automated monitoring and early warning of changes in parameters related to the health and status of animals. The system includes implantable wireless "smart tele-sensor" elements that can be implanted within the animal where they measure, and may transmit, temperature and other parameters (e.g., blood oxygen, accelerations, vibrations, heart rate) related to the health and status of the animal being monitored. Optional relay elements may comprise simple transponders to boost the signals from the smart sensor elements and retransmit processed results. The system includes devices for alerting personnel responsible for care of the animals and identifying the animal needing attention. Installation tools include optional capabilities to program the smart sensor elements to adapt to animal type, season, diet, or other user needs, and to read and correlate electronic and machine read data with human readable animal identification (e.g., ear or collar tags).

None of the above solutions adequately address laboratory animal research applications using mobile animals and more particularly, the prior art fails to adequately provide and efficient a noninvasive photoplethysmographic sensor platform for mobile animals such as small rodents, namely rats and mice.

It is an object of the present invention to address the deficiencies of the prior art discussed above and to do so in an efficient, cost effective manner.

SUMMARY OF THE INVENTION

The various embodiments and examples of the present invention as presented herein are understood to be illustrative of the present invention and not restrictive thereof and are non-limiting with respect to the scope of the invention.

According to one non-limiting embodiment of the present invention, a noninvasive photoplethysmographic sensor platform for mobile animals such as small rodents, namely rats and mice, is provided on an adjustable animal collar. The collar based sensor platform is useful in research, particularly in a laboratory environment when utilizing mobile (e.g. un-anesthetized) animals. The collar is an easily affixed, adjustable attachment mechanism that encircles the animal, such as the neck. The neck of the animal provides several particular advantages. For pulse oximetry measurements this location will provide significant blood flow under all conditions. For small mammals, such as rats and mice, transmittance pulse oximetry through the neck of the subject remains possible. The neck mounted collar offers inherent bite resistance to the sensor platform.

According to one non-limiting embodiment of the present invention, a noninvasive photoplethysmographic sensor platform for mobile animals comprises a body encircling collar configured to encircle a subject animal body portion; a latching member on the collar to secure the collar around the animal; an emitter on the collar configured to be mounted adjacent the subject animal, the emitter having two light sources of distinct wavelengths; and a receiver on the collar configured to be mounted adjacent the subject mammal for detecting light from the emitter that has been toward tissue of the subject mammal.

The body encircling collar may be configured to fit around the neck of a mouse or rat, alternatively the body encircling collar may be configured to fit around the wrist (e.g. above the paw) of an animal, such as a rabbit. The noninvasive photoplethysmographic sensor platform for mobile animals may further include a collar cable extending from the emitter and the receiver on the collar. The noninvasive photoplethysmographic sensor platform for mobile animals may further include a rotation coupling attached to the collar cable and may include a controller cable attached to the rotation coupling, wherein the rotation coupling allows relative rotation between the controller cable and the collar cable. The noninvasive photoplethysmographic sensor platform for mobile animals may further include a controller coupled to the collar cable, wherein the controller is configured to perform pulse oximetry calculations based upon the light detected by the receiver. The noninvasive photoplethysmographic sensor platform for mobile animals may further include a transmitter on the collar coupled to the emitter and the receiver. The noninvasive photoplethysmographic sensor platform for mobile animals may further include at least one further physiologic parameter sensor mounted on the collar. The noninvasive photoplethysmographic sensor platform for mobile animals may provide that the latching member is adjustable and may be configured to secure the collar around the animal in at least one of a plurality of latching positions associated with different effective lengths of the collar.

According to one non-limiting embodiment of the present invention, a method of obtaining noninvasive photoplethysmographic measurements from an animal comprises the steps of: providing a body encircling collar configured to encircle a portion of the body of a subject animal, the collar including a latching member on the collar to secure the body around the neck of the animal, and an emitter on the body configured to be mounted adjacent the subject animal, the emitter having two light sources of distinct wavelength, and a receiver on the body configured to be mounted adjacent the subject mammal for detecting light from the emitter that has been toward tissue of the subject mammal; securing the collar onto the animal with the latch; and obtaining photoplethysomgraphic measurements from the receiver on the collar on the un-anesthetized animal.

The method of obtaining noninvasive photoplethysmographic measurements may have the animal as a rat or a mouse. The method of obtaining noninvasive photoplethysmographic measurements may have the collar secured around the neck of the animal. The method of obtaining noninvasive photoplethysmographic measurements may include the step of obtaining further physiologic measurements from at least one additional sensor mounted on the collar. The method of obtaining noninvasive photoplethysmographic measurements according may provide that the photoplethysmographic measurements are pulse oximetry measurements.

These and other advantages of the present invention will be clarified in the description of the preferred embodiments taken together with the attached figures.

DESCRIPTION OF THE PREFERRED EMBODIMENTS

In summary, the present invention relates to a noninvasive photoplethysmographic sensor platform 10 for mobile animals, such as rats and mice that are utilized in a laboratory environment. Photoplethysmographic measurements on laboratory animals have most often been accomplished on restrained and/or anesthetized animals. This limits the research than can be conducted. Further, in the pulse oximetry field there has been a lack of adequate photoplethysmographic sensors for small mice (and even small rats), until the advent of the Mouse OX™ brand pulse oximeters by Starr Life Sciences in 2005. Prior to this development, commercially available pulse oximeters could provide heart rate data up to about 350 or 450 beats per minute (and even this range required special software modifications for some sensors), which were basically suitable for rats but not small mice given that the small mouse will have heart rates in the range of 400 to 800 beats per minute. The Mouse OX™ brand of pulse oximeters for small rodents has an effective range up to about 900 beats per minute as of 2008 models which has opened up a wider selection of subjects for this type of research.

Figure 1:
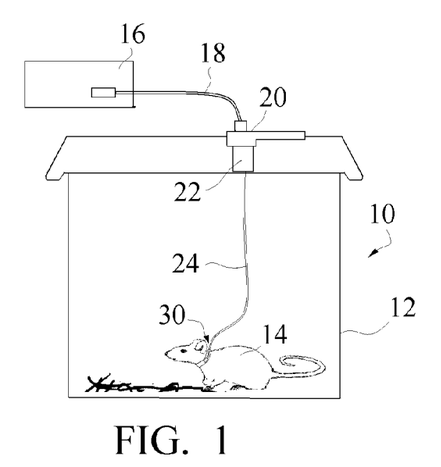
FIG. 1 is a schematic representation of a noninvasive photoplethysmographic sensor platform for mobile animals such as small rodents, namely rats and mice, in accordance with one embodiment of the present invention.
Figure 2:
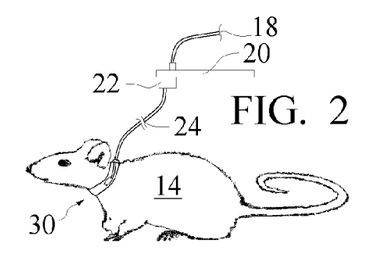
FIG. 2 is an enlarged schematic representation of the noninvasive photoplethysmographic sensor platform of FIG. 1.
Figure 3:
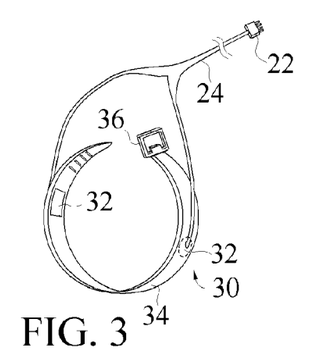
FIG. 3 is an enlarged schematic representation of the noninvasive photoplethysmographic sensor platform of FIG. 2 with the platform in the open position and the animal removed for clarity.
Figure 4:
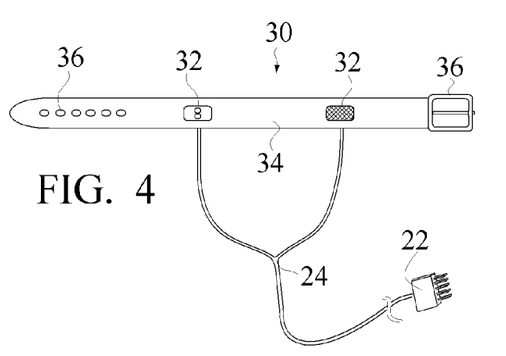
FIG. 4 is a schematic plan view of the noninvasive photoplethysmographic sensor platform of FIG. 2.

FIG. 1 is a schematic representation of a noninvasive photoplethysmographic sensor platform 10 for mobile animals such as small rodents, namely rats and mice, in accordance with one embodiment of the present invention. The platform 10 is particularly well suited for use in a laboratory environment in which a subject animal, such as a mouse 14, is often maintained within a confinement unit 12 (e.g. a cage, cell, housing, etc). The confinement unit 12 is used herein as a generic term for anything holding the subject animals. The unit 12 could be an integral element of the research, such as a maze or other structured test environment. The unit 12 will often be a housing area for the animal. The details of the unit 12 will be well known to those of ordinary skill in animal research fields.

The subject animal may be any subject animal for which photoplethysmographic measurements are desired. A large amount of laboratory research is conducted on rats and mice, however photoplethysmographic measurements has been of limited availability to the researchers when using such subjects. Consequently, the present invention has particular application to research associated with rats and mice. More accurately the present invention provides particular advantages and expands potential research possibilities when utilized with subjects of the order rodentia, and even more precisely, when utilized with the sub-order muroidia. A particularly advantageous aspect of the present invention is that the platform 10 allows for photoplethysmographic measurements from a mobile animal. The mobile animals may still be retrained by the confinement unit 12, but the animals may still have a certain range of motion therein. There is nothing that prevents the platform 10 from being effectively utilized for restrained and/or anesthetized animals either.

The platform 10 will include a processor or controller 16 coupled thereto. The controller 16 is shown schematically in FIG. 1 and can be formed as a component of a laptop or desktop computer. The controller 16 may be the combination of stand alone hardware and software that is coupled with computer for the user interface, display memory and some computation. One particularly advantageous use of the photoplethysmographic measurements of the platform 10 is for pulse oximetry, particularly in animals such as rats and mice 14. In this application the controller 16 is the commercially available Mouse OX™ product from Starr Life Sciences with the unique sensor mounting and coupling as described hereinafter. The details of the controller 16, including the user interface, the user display, memory or the like is not discussed herein in detail.

A conventional controller cable 18 extends from the controller 16 for transmitting control and power signals from the controller and data back to the controller 16. The controller cable is coupled to a rotation coupling 20, also called a swivel link. A collar cable 24 is attached to and extends from the rotation coupling 20 through attachment plug 22. The rotation coupling 20 allows relative rotation between the controller cable 18 and the collar cable 24. The rotation coupling 20 provides a convenient location for mounting to the confinement unit 12. The use of the swivel link or rotation coupling 20 allows the animal, e.g. mouse 14, to be effectively freely roaming within the area of the unit 12, wherein twisting of the cables is avoided. The swivel link or rotation coupling 20 also serves to effectively divide the platform 10 into an animal specific portion or base 30 and the controller 16, whereby the controller 16 can be easily used with a large number of animal specific portions 30 in a serial fashion. Further, it allows for easy replacement of the portion or base 30 which is anticipated to have a shorter life span than the controller 16.

The present invention does anticipate that the controller 16 may be simultaneously (e.g. a parallel attachment) connected to a number of animal specific portions or bases 30 through separate cables 18 to allow for obtaining numerous study results at the same time, but this configuration does not eliminate the advantages of the coupling 20.

The portion or base 30 includes sensors 32 mounted on a body encircling collar 34 configured to encircle a subject animal body portion, such as, specifically around the neck of the subject animal. The neck of small mammals such as rats and mice allows for a number of advantages for photoplethysmographic pulse oximetry measurements. The necks of animals of the sub-order muroidia tend to allow for both transmittance and reflective pulse oximetry measurements. Transmittance pulse oximetry is where the received light is light that has been transmitted through the perfuse tissue, whereas in reflective pulse oximetry the representative signal is obtained from light reflected back from the perfuse tissue. Each technique has its unique advantages. Transmittance techniques often result in a larger signal of interest, which is very helpful in small animals that have very small quantities of blood being measured to begin with. Reflective techniques can be used in environments that do not allow for transmittance procedures (e.g. the forehead of a human).

Further, the neck region of the animal offers an area with a relatively large blood flow for the animal, which will improve the accuracy of the measurements. In addition to increased blood flow, the blood flow is present under substantially all conditions. In other areas of the animal, such as the legs, paws and tail, the animal will often cut off blood flow under a variety of conditions. For example if the animal is cold or sufficiently agitated the blood flow to the tail can be shunted. The neck, in contrast represents an area of the animal that will always maintain a constant blood flow for measurements.

The neck collar 34 also provides a bite proof location for the sensor mounting. In attempting to remove the sensors 32 the biting of most animals, particularly animals of the sub-order muroidia, will be stronger than the clawing, and the neck location prevents the biting attacks as the animal cannot reach the collar 34. A secured collar 34 cannot be removed by the animal's paws or clawing.

An alternative location within the scope of the present invention is around the torso, abdomen or chest, of the animal subject. These locations offer some particular advantages and disadvantages. These locations may not provide the same "bite proof" advantages of the neck mounting discussed above, but offer unique pulse oximetry data for small rodents. For example, adding multiple sensors 32 in a chest mounted arrangement would allow for a calculation of the oxygenation of the returning blood through multiple measurements through the heart region. Further the abdomen and the chest mounting will not experience blood shunting that can prevent accurate results. Further these locations present particularly advantageous mounting locations for additional sensors, such as accelerometers, EKG leads, temperature sensors and the like.

An alternative location within the scope of the present invention is placing the collar 34 around the head of the animal subject with measurements through the head of the animal. The head mounting provides the advantage of being bite proof. It also allows measurements by directing the light through the ears across the head of the animal, which is not a possibility in humans or other large mammals. Further the head mounting allows the sensors to also use the eyes to transmit light through in a reflective or transmittance type system. The head mounting application may be less applicable for free roaming subjects, but offers certain advantages.

The form and material of the collar 34 can be any of a wide variety of materials and shapes. Essentially any suitable construction from the field of radio-telemetry collars and animal collars (e.g. pet collars) can be utilized if sized to fit the subject animals. It is anticipated that the collar 34 includes a releasable latching member 36, such as a buckle and associated holes, to secure the collar in position around the animal neck. The buckle type is an example of an adjustable latching member 36 that is configured to secure the collar around the animal, such as mouse 14 in at least one of a plurality of latching positions, defined by holes, associated with different effective lengths of the collar 34. Other adjustable latching members are possible, such as a zip-tie attachment (commonly used as cable ties) and slide buckle arrangement (popularized with backpack straps). With the adjustable latching member 36 the collar 34 is suitable for a given range of animal sizes.

The sensors 32 include an emitter on the collar 34 configured to be mounted adjacent the subject animal, mouse 14, with the emitter having two light sources of distinct wavelengths; and a receiver on the collar 34 configured to be mounted adjacent the subject mammal for detecting light from the emitter that has been toward tissue of the subject mammal. The emitter and receiver may be configured for transmittance operation as shown, or even reflective operation as noted above.

The advantages of the platform 10 include the location of the sensors 32 as discussed above. Further, this platform 10 allows the measurements to be obtained from a mobile animal, which will be free to roam about the confinement unit 12, for the neck, torso and certain head based applications of the sensors 32. Neither the collar 34 nor the collar cable 24 will limit motion in this area, and the swivel link prevents cable twisting from interfering with animal motion. This opens the door for researchers to collect photoplethysmographic measurements, in particular pulse oximetry measurements, under a greater number of conditions.

It is understood that motion of the animal can disrupt the reliability of photoplethysmographic pulse oximetry measurements. The commercially available Mouse OX™ system, which has been used for thigh and tail sensor mounted applications for restrained or anesthetized animals, has developed motion artifact rejection techniques to avoid inaccurate readings associated with tail or paw motion or the like. This motion artifact data rejection technique becomes even more important with mobile animals. Further, the existing techniques are sufficient to allow for reasonable number of readings in a mobile animal.

Additional techniques for improving photoplethysmographic pulse oximetry measurements in mobile subjects could be helpful. For example, adding an accelerometer sensor (see 42 of FIG. 6) on the collar 34 will allow more information to the researcher and this information can be combined with the pulse oximeter measurements so the controller will be able to match periods of rapid acceleration with the pulse oximeter measurements as a method of identifying potentially anomalous readings. Other additional sensors, such as pressure transducers, strain gauges, resistance sensors, can be added to supply additional data that can be used to cross check and to correlate the pulse oximetry data.

Figure 5:
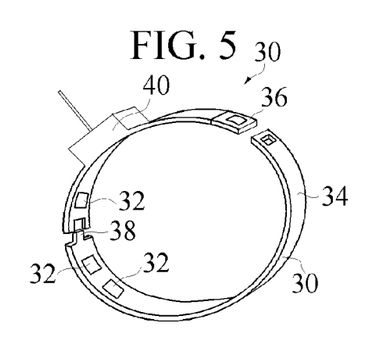
FIG. 5 is a schematic perspective view of a noninvasive photoplethysmographic sensor platform according to another embodiment of the present invention.

FIG. 5 illustrates a different collar 34 that replaces the collar cable 24, link 20 and cable 18 with a wireless transmitter/receiver 40 for wireless operation. Controller 16 would similarly have a wireless transmitter/receiver 40 to complete the link. Wireless technology, in general, and radio-telemetry on collars for wildlife studies is very well established and the details need not be discussed further. Wireless operation will generally allow for more freedom of mobility to the animals. It is apparent that the wireless operation allows for wildlife applications in research, or completely free roaming animals.

FIG. 5 also illustrates the use of multiple sets of sensors 32, and this one is set up to utilize both a reflective and a transmittance pulse oximeter arrangement. This dual sensor approach allows the controller 16 to cross validate the results to obtain a more accurate measurements and provide measurements more often.

Figure 6:
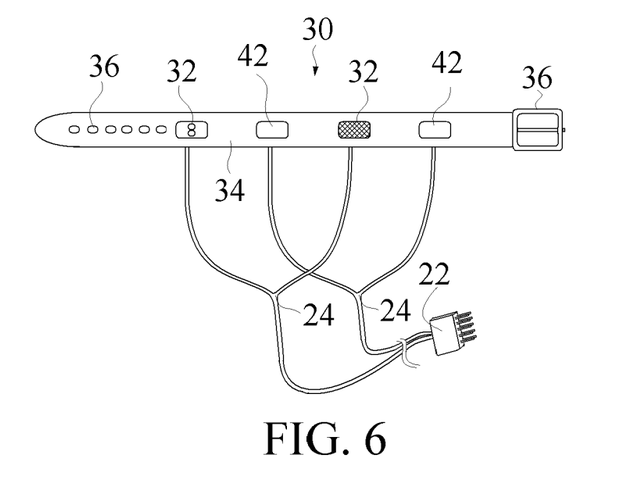
FIG. 6 is a schematic plan view of a noninvasive photoplethysmographic sensor platform according to another embodiment of the present invention.
Figure 7:
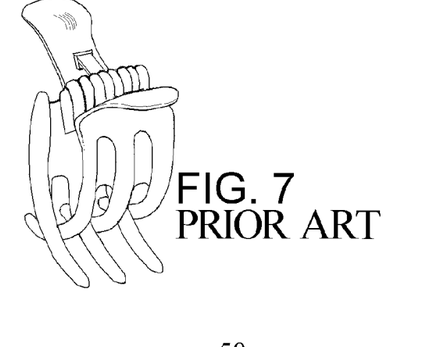
FIG. 7 is a perspective view of a prior art hair clip that is illustrative of the function of a noninvasive photoplethysmographic sensor platform according to another embodiment of the present invention.
Figures 8, 10:
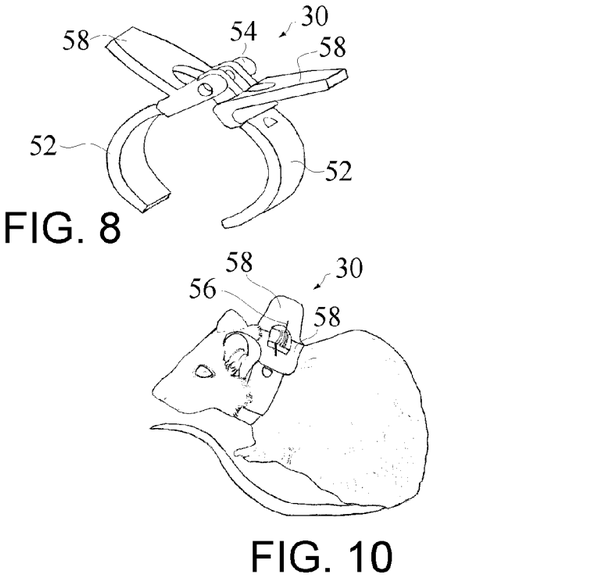
FIG. 8 is a perspective schematic view of a noninvasive photoplethysmographic sensor platform clip according to another embodiment of the present invention.
FIG. 10 is a perspective view of a neck based application of the noninvasive photoplethysmographic sensor platform according to FIGS. 8-9.

As noted above the platform 10 is not limited to sensors 32 for photoplethysmographic measurements. Additional sensors 42 can be added, such as temperature sensors, accelerometers, and other physiologic and environmental sensors as shown in FIG. 6. These sensors 42 can have their data utilized by the controller 16 to validate the obtained data of sensors 32, and vice versa. The particular validation methodologies will depend on the particular sensors. As a representative example, high accelerometer readings would be associated with rapid animal motion and is a clear flag to question the pulse oximeter measurements during such changes.

The sensors 42 need not operate completely alone. For example a visible light can be a sensor 42 which is combined with a time elapsed camera on the top of the unit 12, and together will form a time stamped motion tracking sensor unit.

The advantages of collar 34, neck, head and torso based photoplethysmographic pulse oximetry measurements are described above, particularly in connection with animals of the sub-order muroidia. However, the collar 34 and sensors 32 are not limited thereto. The collar 34 may be placed on the wrist or above the paw of certain animals, particularly larger animals such as rabbits, monkeys, dogs, cats, etc. It is very important to note that in use with such other applications, the controller 16 and associated elements must be practical for such applications. As has been found in the past when others have attempted to make mere software changes to adapt a human oximeter for small animal research, software changes alone cannot stretch a hardware system from one base of operation to another. The LED drivers, the sampling rates the amplifiers, the noise cut of filters, and the like must all be practical and effectively intended for the desired operation. In other words, a collar 32 that physically fits around the paw of one species and the neck of another may NOT be interchangeable for both such purposes as it likely will not obtain meaningful data in both applications. Consequently, collars 34 made under the present invention will likely be configured for particular applications such as a neck collar for small rats and mice within a given neck size (likely listed as weight of the animal), or a wrist collar for dogs and cats within a given weight range, or a chest collar for small rats and mice within a given size, etc.

Neck Collar clip concept development and features and benefits.

The base 30 may be formed as neck collar clip 34' as another version of the wraparound neck collar of the present invention described above. The advantage of this design is a simple one handed application to the neck of an animal by only a single user.

The reason for applying the clip 34' specifically to the neck is that the brain is the last organ to have blood flow reduced in response to some sort of physiologic challenge, such as cold, stress or blood loss, which can cause a shock response. In the case of shock, blood flow is reduced to the extremities, but is still always supplied to the brain, and that blood must necessarily pass through the neck. Additionally, because of the continuous flow of blood through the neck to the brain, it is not necessary to heat the animal to aid perfusion, as can be the case for measurements on the tail or the extremities.

Researchers prefer not to heat their animals in order to make oximetry-based measurements, and a clip location on the neck provides the best opportunity to allow that. Another advantage of the neck is that it is difficult for a mouse in particular, to be able to remove a clip 34' from its neck because it cannot easily be reached. More importantly, the animal cannot chew on the clip 34' itself or the attached sensor pads 32 when the clip 34' is attached to its neck. There is no other position on the body of a mouse that provides such an advantage.

The clip 34' can be designed to be light and unobtrusive, thus it also can be used to make measurements on conscious animals that are free-roaming within the boundaries of the attached wire 24. This boundary can be circumvented by applying a form of rotary switch/commutator 20 in the wiring pathway to allow the animal to spin without losing electrical connectivity between the sensors 32 and the control unit 16.

One of the most important benefits for researchers of this design over other types of sensor shapes and forms is that it can be applied very quickly, by one person, on an un-anesthetized animal. This allows someone to apply it quickly without help, and be able to obtain measurements almost immediately, greatly increasing the throughput of animals over sensor types that require anesthesia to apply, require loading the animal in some sort of restraint device or require heating the animal and waiting for sufficient perfusion in order to make measurements.

The clip 34' is designed to have two halves 52 that are connected with a pin 54 at the top pivot point or hinge. A torsion spring 56 is positioned by passing the pin 54 through it so that it resides between the clip halves 56 and can leverage off of both clamp handles 58. The LED(s) 32 and photodiode(s) 32 reside opposite each other on the inside of the clip 34' as shown in the FIGS. 9 and 11. The wires 24 protrude through holes 60 in the handles 58 of the clip 34' and pass to a connector 22 that eventually attaches to a wire harness to connect it to the oximeter control box 16.

Researchers may be concerned that a clip 34' could in some manner choke their animals, the clip 34', for certain applications, can also be designed so that when it is placed on an animal, it does not wrap all the way around the neck, preventing pressure from being applied directly to the trachea.

Figure 9:
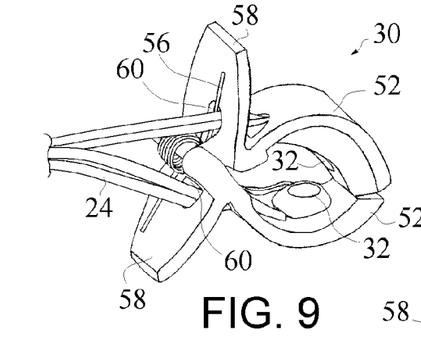
FIG. 9 is a perspective view of a noninvasive photoplethysmographic sensor platform base using the clip of FIG. 8.
Figure 11:
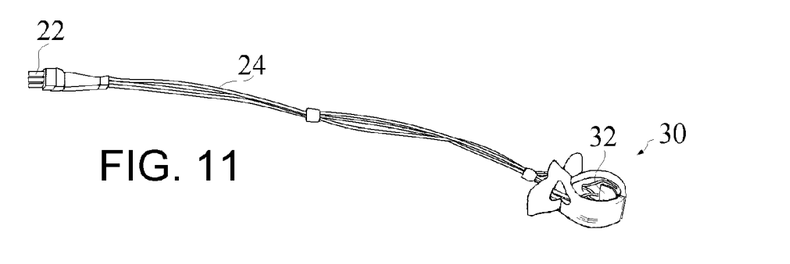
FIG. 11 is a perspective view of the noninvasive photoplethysmographic sensor platform according to FIGS. 8-10.

In the FIGS. 9 and 11, the photodiode 32 resides on the opposite clip half 52 from the LED 32 for transmission measurements, but the lighting components or sensors 32 could also reside on only one side of the clip 34' and operate in a reflectance mode.

The clip 34' can be designed to accommodate more than 1 LED and/or more than 1 photodiode in order to allow more light for transmission through thick necks, or necks with dark fur. The goal is to eliminate shaving the animal, something that requires delivery of anesthesia to the animal and is time-consuming for the researcher.

Another way to improve light transmission is to use this clip 34' in conjunction with coupling gel, or to line the components or sensors 32 with a type of sticky gel that would act like an optical coupling gel, but also provide a measure of adhesion to hold the clip in place. Such a gel would also render the design more disposable.

Regarding being able to hold the clip 34' on the animal, a proper shape in conjunction with ample spring 56 force may be sufficient to maintain the position of the clip 34' even while the animal is moving. However, this clip 34' is intended to be used on animals that are freely moving, possibly requiring more adhesion than a simple spring force and shape can provide. One solution is to apply a type of adhesive around the animal contacting surfaces, or at points along the animal contacting surfaces, to aid adhesion and to stabilize the clip 34' to the animal.

The clips 34' could also be made of different colors to allow identification of such clips 34' designed for different functions or animal types. Moreover, sections of the clip 34' could be made opaque or translucent, depending on the need to block ambient light from reaching the testing location.

In the clip 34' design described above, the LED and photodiode sensor pads 32 are adhered to the inside of the clip 34' as individual components. Wires are then soldered to these components and passed through holes 60 in the clip handles 58. The other ends of the wires are then soldered to a connector of some sort. An alternate approach is to use a mylar (or other material) strip in which the components are embedded, with electrical connections made using conductive traces to a connector on the end. This strip could then be adhered in some manner to the inside of the clip 34' so that no gluing or soldering would be necessary. It would also provide a disposable element for the clip 34' assembly. Such a configuration would greatly reduce the manufacturing time of the clip 34', by eliminating all of the work associated with gluing the components, fishing wire leads, then soldering both to the components, then to the connector.

Figure 12:
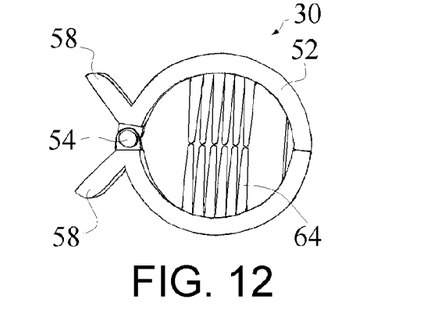

It has been found to be quite difficult to pass light through dark fur because dark colored hair or fur absorbs light in the red wavelength region. However, the absorptive effect of the hair can be reduced by combing the fur against the direction that it naturally lays to expose the skin underneath. One way to do this is to fashion a clip 34' that has combing teeth 64 that can be used to push the fur forward. An exaggerated example of such a comb 64 is shown in FIG. 12. In this figure, the tines 64 are about 5 times longer than might be optimal for use as a short comb. The user can apply this clip 34' as one would normally, but could pull the clip 34' forward toward the head of the animal when attaching it, to comb the hair forward, exposing the skin underneath.

The collar-type clip 34' described here does not need to be limited to use only on the neck. By designing a larger version with appropriate shape, it could be placed on the chest and/or belly of an animal. Use on the belly would improve breathing signals because of the breathing motion that is amplified in the belly region. On the chest, one has access to the cardiac chambers and the large systemic arteries. There is also access to the pulmonary artery, which presents a unique opportunity to make saturation measurements on truly mixed venous blood, because a mouse is small enough to shine light across its chest. The pulmonary artery carries purely mixed venous blood to the lungs, and because it is the conduit that leaves the right ventricle, it is the one location in the body where not just venous blood is pulsating, but mixed venous blood. By measuring pulmonary artery saturation, and making a normal systemic arterial saturation somewhere else, one could calculate the arterio-venous gradient (the A-V gradient within this application), an important metabolic measurement not heretofore available with non-invasive pulse oximeters.

A further embodiment of a neck clip is a clip configuration in which the LED and photodiode sensors reside across from each other, but they have protrusions on their faces that can be directed into the ear holes of an animal. Such a configuration would look like a set of headphones, but the sensor elements would protrude like ear buds into the end of either ear canal, to hold the assembly in place under some slight spring tension.

Whereas particular embodiments of the invention have been described above for purposes of illustration, it will be evident to those skilled in the art that numerous variations of the details of the present invention may be made without departing from the spirit and scope of the present invention.

What is claimed is:

1. A method of obtaining noninvasive photoplethysmographic measurements from an animal, which is a mouse or a rat, comprising the steps of:
    Providing a body encircling base configured to encircle one of the head, neck, chest or abdomen portion of the body of a subject animal, which is a mouse or a rat, the base including an emitter on the body configured to be mounted adjacent the subject animal, the emitter having two light sources of distinct wavelength, and a receiver on the body configured to be mounted adjacent the subject animal for detecting light from the emitter that has been toward tissue of the subject animal;
    Securing the base in a position encircling one of the head, neck, chest or abdomen portion of the body of a subject animal, which is a mouse or a rat;
    Obtaining photoplethysomgraphic measurements from the receiver on the base on the subject animal which is a mouse or a rat.

2. The method of obtaining noninvasive photoplethysmographic measurements according to claim 1 wherein the animal is an anesthetized rat or an anesthetized mouse.

3. The method of obtaining noninvasive photoplethysmographic measurements according to claim 1 wherein the base is secured around the neck of the animal.

4. The method of obtaining noninvasive photoplethysmographic measurements according to claim 1 wherein the base is secured around the chest of the animal.

5. The method of obtaining noninvasive photoplethysmographic measurements according to claim 4 further including providing additional sensors at a location other than the base making a normal systemic arterial saturation measurements, and calculating an A-V gradient about the subject animals heart.

6. The method of obtaining noninvasive photoplethysmographic measurements according to claim 1 further including the step of obtaining further physiologic measurements from at least one additional sensor mounted on the base.

7. The method of obtaining noninvasive photoplethysmographic measurements according to claim 1 wherein the base is secured around the head of the animal.

8. The method of obtaining noninvasive photoplethysmographic measurements according to claim 7 wherein the emitter is adjacent the eyes of the animal.

9. The method of obtaining noninvasive photoplethysmographic measurements according to claim 1 wherein the body encircling base is formed as a neck collar clip secured around the neck of the animal.

10. The method of obtaining noninvasive photoplethysmographic measurements according to claim 9 wherein the neck collar clip has two halves coupled together at a pivot pin.

11. The method of obtaining noninvasive photoplethysmographic measurements according to claim 1 further including the step of calculating an A-V gradient about the subject animals heart.

12. The method of obtaining noninvasive photoplethysmographic measurements according to claim 11 wherein the animal is an anesthetized rat or an anesthetized mouse.

13. The method of obtaining noninvasive photoplethysmographic measurements according to claim 11 further including a transmitter on the base coupled to the emitter and the receiver.

* * * * *